United States Patent [19]

Serra et al.

[11] Patent Number: 5,681,335
[45] Date of Patent: Oct. 28, 1997

[54] MINIATURIZED BRUSH WITH HOLLOW LUMEN BRUSH BODY

[75] Inventors: R. J. Serra, Irvine; Blair D. Walker, Long Beach; Scott M. Evans, Santa Ana, all of Calif.

[73] Assignee: Micro Therapeutics, Inc., San Clemente, Calif.

[21] Appl. No.: 509,354

[22] Filed: Jul. 31, 1995

[51] Int. Cl.$^6$ .................................................. A61B 17/22
[52] U.S. Cl. ............................................ 606/159; 128/756
[58] Field of Search ........................ 128/756; 606/159, 606/170, 171, 181, 167, 180

[56] References Cited

U.S. PATENT DOCUMENTS

| | | | |
|---|---|---|---|
| 3,613,664 | 10/1971 | Willson et al. | 128/756 |
| 5,370,653 | 12/1994 | Cragg | 606/170 |
| 5,456,265 | 10/1995 | Yim | 128/756 |

FOREIGN PATENT DOCUMENTS

3921071 A1  2/1991  Germany ............ A61B 17/22

*Primary Examiner*—Michael Buiz
*Assistant Examiner*—Kevin Truong
*Attorney, Agent, or Firm*—Joseph F. Breimayer

[57] ABSTRACT

A miniaturized brush and method of making same having a hollow lumen for introducing an agent for dissolving a soft fibrinous obstruction, such as a recently formed thrombus, within a patient's vascular system. The brush has soft, flexible bristles extending outward from the drive shaft distal section, the bristles being sufficiently resilient and dimensioned for enabling compression and passage of the brush out of and back into the distal end of an introducer lumen and to mix into the fibrin of the soft thrombus, yet not damage the vessel wall. The brush assembly is formed of a proximal section comprising an elongated proximal tube and a distal section comprising a distal tube extension, the proximal and distal sections having an aligned lumen and forming a drive shaft or brush body. The brush is formed of brush bristles entrapped between coiled wire turns of a metal having enhanced radiographic imaging characteristics wound about the outer wall of the distal tube extension and distributed in a uniform pattern or in a helical pattern around the circumference of the outer wall to form a helical brush. The distal tube extension may be a continuation of the elongated proximal tube and the coiled wire may be wound about the outer wall of the proximal tube. Alternatively, a separate distal tube extension may be attached to a reinforced proximal tube and the coiled wire may be wound about the distal tube extension and a portion of the distal end of the proximal tube.

27 Claims, 8 Drawing Sheets

MINIATURIZED BRUSH WITH HOLLOW LUMEN BRUSH BODY

BACKGROUND OF THE INVENTION

1. Field of the Invention

The present invention relates to a miniaturized brush formed at the distal end of an elongated brush body having a hollow lumen formed therein and particularly to the fabrication thereof and the use thereof in medical and other applications.

2. Description of the Background Art

A thrombectomy system for dissolving a soft fibrinous obstruction, such as a recently formed thrombus, within a patient's vascular system, either in a patent vein or artery or in a prosthetic implant, employing a soft rotating brush for separating and mixing the fibrin of the thrombus while a dissolving agent, e.g. streptokinase or urokinase, is introduced and mixed in and applied to the separated fibrin is disclosed in commonly assigned, U.S. Pat. No. 5,370,653, incorporated herein by reference in its entirety. The brush has soft, flexible bristles extending outward from the drive shaft distal end. The brush is attached to an elongated, flexible, rotatable drive shaft or brush body which is attached at its proximal end to a drive motor to impart rotary motion to the drive shaft and brush. The system includes an introducer catheter adapted to be introduced and advanced through a patient's blood vessels until the distal end is positioned adjacent the soft fibrinous thrombus.

Once the introducer catheter is positioned, the brush and drive shaft are passed through the introducer catheter lumen and out its distal opening to place the brush in contact with the soft thrombus. The bristles are sufficiently resilient and dimensioned for allowing compression and passage of the brush out of and back into the distal opening of the introducer lumen and for mixing into the fibrin of the soft thrombus, without damaging the vessel wall. The dissolving agent is introduced during rotation of the brush either through the introducer catheter lumen or a drive shaft lumen and out exit ports at the distal ends thereof in the region of rotation of the brush for dissolving the soft thrombus as it is contacted by the bristles.

In one embodiment described in the '653 patent, the drive shaft is hollow to allow the transmission of the dissolving agent from the proximal end source to the exit ports. Optionally, a balloon catheter or a mesh basket may be coaxially introduced through the drive shaft lumen and placed distally to restrain the flow of fragments distally and to allow the dissolving agent to complete the dissolution thereof. The hollow lumen also allows the introduction of the brush over a previously introduced and positioned guide wire so that the brush may be readily advanced to a thrombus in a blood vessel.

The miniaturized, hollow lumen drive shaft for a brush of the type described in the '653 patent is highly desirable. No particular construction of the hollow lumen drive shaft to achieve small overall diameter is described in the '653 patent.

SUMMARY OF THE INVENTION

In view of the apparent interchangeable use in the background art, only the terms soft fibrinous obstruction or thrombus and thrombectomy will be employed in the remaining description of the invention and the claims, and it will be understood that these terms shall embrace and be the equivalent of blood clot or embolus and embolectomy, respectively, and are applicable to the removal of soft, recently formed thrombi or blood clots.

It is a principal object of the present invention to provide a hollow lumen, thrombectomy brush and method of fabrication which allows for the brush to be introduced over a previously placed guide wire into a very small blood vessel.

It is a further principal object of the present invention to provide such a hollow lumen, thrombectomy brush and method of fabrication which provides for a brush drive shaft that is capable of transmitting torque from the proximal end thereof to the distal brush to effectively rotate the brush despite the extension of the drive shaft through a convoluted and tortuous blood vessel pathway.

It is yet another object of the present invention to provide an enhanced method of fabricating such a hollow lumen, small outer diameter, high torque drive shaft and brush assembly.

It is still a further object of the invention to provide such a miniaturized brush and method of fabrication for uses in other medical applications than thrombectomy and for non-medical fields and uses where a miniaturized brush with a hollow lumen would find particular utility.

In accordance with these and other objects, a miniaturized brush assembly is provided with an elongated, flexible, rotatable drive shaft adapted to be attached at its proximal end to a drive motor for rotating the shaft, the drive shaft being formed in a proximal elongated section of a hollow, thin wall tube having an inner lumen and an outer surface and a distal section comprising a hollow, thin wall tube extension and a coiled wire wound about the hollow tube extension and entrapping brush filaments between turns of the coiled wire and the outer wall of the hollow tube extension forming the distal section.

In a first, continuous tube embodiment, the proximal elongated section and the hollow tube extension are fabricated of a single, continuous, elongated, thin wall tube, and the coiled wire is wound continuously over the elongated tube from the proximal to the distal end thereof, whereby the continuous coiled wire provides a structural reinforcement to enhance torque transfer from the proximal end to the distal end section and the brush attached thereto.

In a further, joined tube embodiment, the proximal section is fabricated of a proximal, elongated tube having sufficient column strength to be advanced over a guide wire or through an introducer catheter and torque transfer to allow rotation of the distal brush from the proximal end thereof. The proximal tube has a predetermined outside diameter, a proximal tube lumen inside diameter and a constant wall thickness through the majority of its length. A stepped down outer diameter with reduced wall thickness is formed at the distal end portion thereof. The distal section is formed of a separate distal tube extension having an inside diameter corresponding to the inside diameter of the proximal tube lumen. The distal tube extension is expanded or flared to fit over the stepped down outer diameter at the distal end portion of the proximal section at the junction thereof without substantially increasing the junction outside diameter beyond the outside diameter of the proximal tube.

The coiled wire is wound about the hollow distal tube extension and about and entrapping brush filaments between turns of the coiled wire in the distal section. In the joined tube embodiment, the coiled wire is continuously wrapped the length of the distal tube extension, over the junction of the flared distal tube extension and a predetermined distance proximally from the junction. The junction is bonded and sealed by adhesives or heat fusion applied between the entrapping brush filament turns of the coiled wire, the outer walls of the proximal tube distal section, the stepped down outer diameter distal portion of the proximal tube, the flared proximal portion of the distal tube extension, and the distal tube extension.

A bristle winding mechanism is employed to wind wire into the coiled wire configuration over the underlying distal tube section or extension of either embodiment while the distal tube extension lumen is supported on a mandrel. In the joined tube embodiment, the distal tube extension is first attached to the distal stepped end of the braided tube. In either embodiment, the proximal tube section and the distal tube extension are supported in common on an elongated mandrel and inserted into a winding fixture for rotation with respect thereto. The brush bristle filaments are fed into the winding interface of the wire and the tube outer wall as the distal tube extension/section and the mandrel are rotated with respect to the winding fixture. In either embodiment, once the brush length is achieved, the coiled wire may be wrapped distally about the distal end of the distal tube extension outer wall sufficiently to securely terminate the coiled wire.

In all embodiments and variations, the brush filaments may be trimmed to an even length or an uneven length in a desired pattern to provide soft, flexible bristles extending outward from the drive shaft distal end. The bristles are sufficiently resilient and dimensioned for enabling compression and passage of the brush out of and back into the distal end of the introducer lumen and effective to mix into the fibrin of the soft obstruction yet not damage the vessel wall.

In any of the embodiments described above, the distal tube extension may be preformed with weep holes or perforations to allow the dispersion of dissolving agents or other fluids introduced down the lumen while the guide wire is present or after it is withdrawn. The lumen distal end opening may be provided with self sealing flaps to seal about the guide wire while the brush assembly is advanced or to seal the lumen end opening after the guide wire is retracted to ensure that the introduced fluid is dispersed within or proximal to the brush bristles. The distal end opening of the tube extension lumen may alternatively be left open to provide a fluid dispersion or flush operation distal to the brush. These and other features of and methods of use of the brush assembly described in the above-incorporated '653 patent may be employed in the use of the miniaturized brush assemblies of the present invention.

The miniaturized brush assemblies of the present invention provide reduced overall outer diameter easing introduction through small diameter introducer catheter and/or blood vessel lumens. In addition, the thin wall construction provides a drive shaft or brush body lumen with a relatively enlarged inner diameter for introduction over a guide wire and for introduction and passage of fluids therethrough. The drive shaft or brush body in each assembly is reinforced sufficiently to allow advancement through tortuous blood vessel passageways and to provide torque transfer to the distal brush.

BRIEF DESCRIPTION OF THE DRAWINGS

These and other objects, advantages and features of the invention will become apparent from the following detailed description of the preferred embodiments of the invention, in which.

Figure 1:
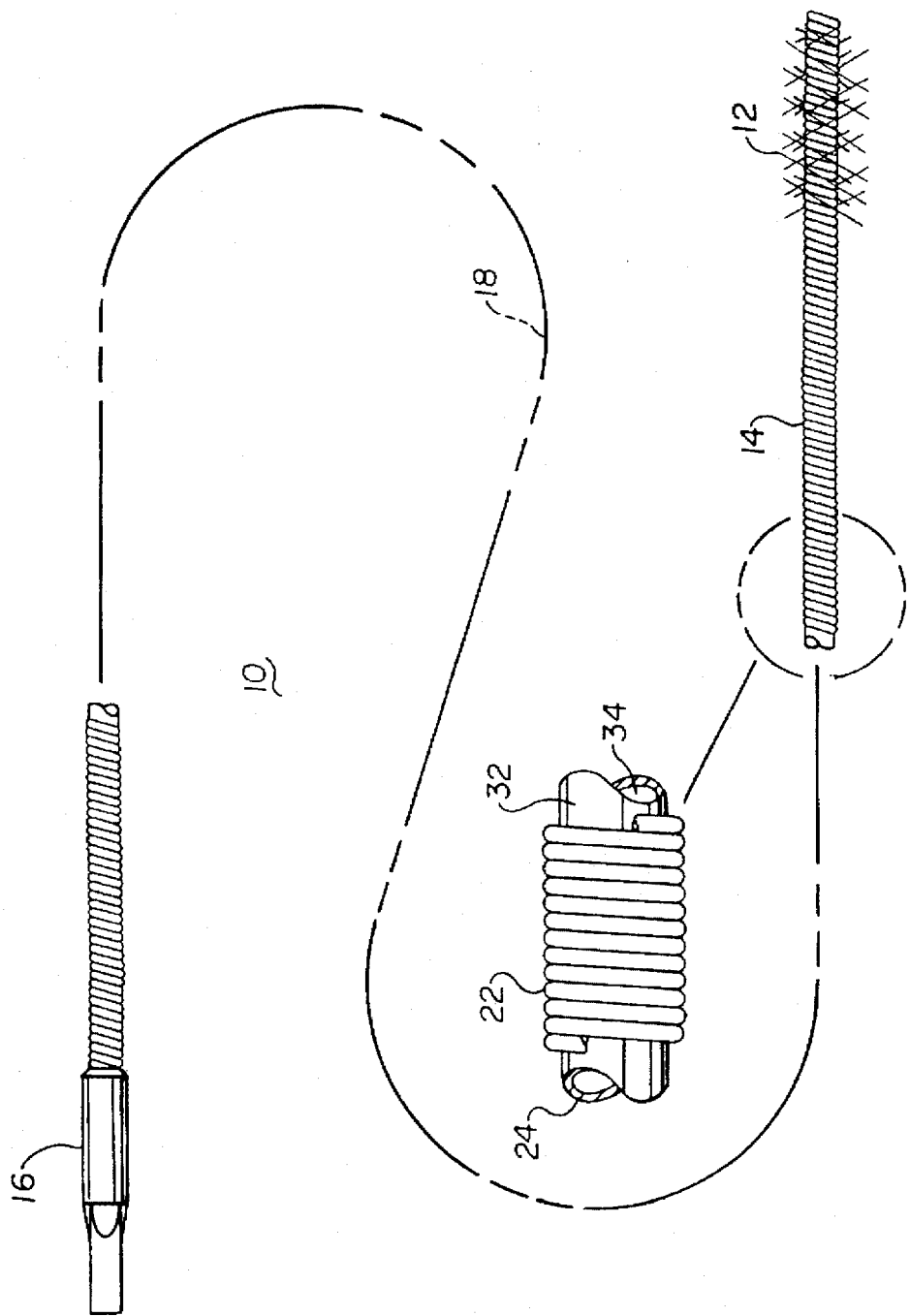
FIG. 1 is a view of the first, continuously wound tube embodiment of the miniaturized brush and drive shaft or body of the present invention.

The drawing figures are not necessarily to scale.

DETAILED DESCRIPTION OF THE PREFERRED EMBODIMENTS OF THE INVENTION

In the following description, the alternative preferred embodiments share common features of the invention which are illustrated in preferred uses described in the above-incorporated '653 patent. Other uses will be apparent from the following description of the construction of the miniaturized brush assemblies.

Figure 2:
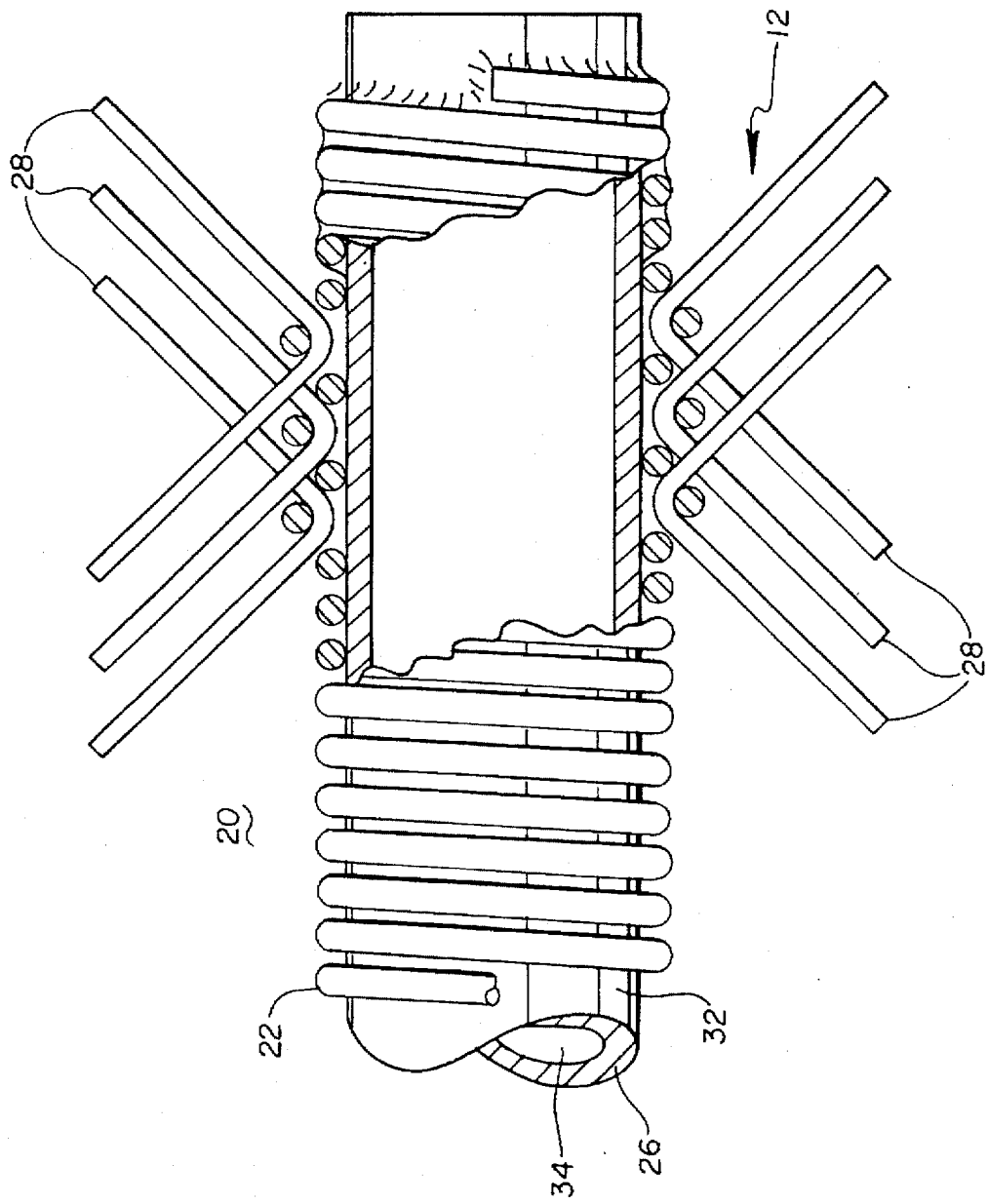
FIG. 2 is an enlarged, cross-section view of the brush of FIG. 1 illustrating the entrapment of brush filaments between turns of the continuously wound coiled wire and over the distal tube section.

Referring to the first, continuous tube embodiment of FIGS. 1 and 2, the brush assembly 10 includes the miniaturized distal brush 12 and brush body or drive shaft 14. The brush body 14 is adapted to be attached at its proximal end drive hub 16 to a drive motor (not shown) for rotating the brush body 14 when it is operated as an elongated, flexible, rotatable drive shaft. The drive shaft 14 is formed in a proximal elongated section 18 of a hollow, thin wall tube 24 having an inner lumen and an outer surface and a coiled wire 22 wound over the outer surface thereof. As shown in greater detail in FIG. 2, a distal section 20 is formed of a hollow, thin wall distal tube extension 26 of thin wall tube 24. The coiled wire 22 is wound continuously over the outer surface of the thin wall tube 24 and the distal tube extension 26. Brush bristles 28 are entrapped between turns of the coiled wire 22 and the outer wall 32 of the hollow distal tube extension 26 forming the distal section 20.

In the first, continuous tube embodiment of FIGS. 1 and 2, the proximal elongated section 20 and the hollow distal tube extension 26 are fabricated of a single, continuous, elongated, thin wall tube 24 having an outer surface or wall 32 and an inner lumen 34. The coiled wire 22 is wound continuously over the surface 32 from the proximal to the distal end thereof. The continuous coiled wire 22 provides structural reinforcement to the underlying thin wall tube 24 and retains the brush bristles 28 in the distal section 20. The combined structure enhances column stiffness and torque transfer from the proximal drive hub end 16 to the distal end section 20 and the brush 12 attached thereto.

The thin wall tube 24 is preferably formed of nylon tubing having an outside diameter of about 0.045 inches, an inside diameter of about 0.038 inches, and a wall thickness of about 0.003 inches. The coiled wire 22 is preferably formed of stainless steel wire having a diameter of 0.003–0.005 inches, and the brush bristles 28 are preferably filaments of nylon having a diameter of about 0.002–0.004 inches. As described below, adhesive or heat setting may be used to bond the turns of the coiled wire 22 to the entrapped brush bristles 28 and the outer wall 32 in the distal section 20, and may also be used at the proximal end drive hub 16.

Figure 3:
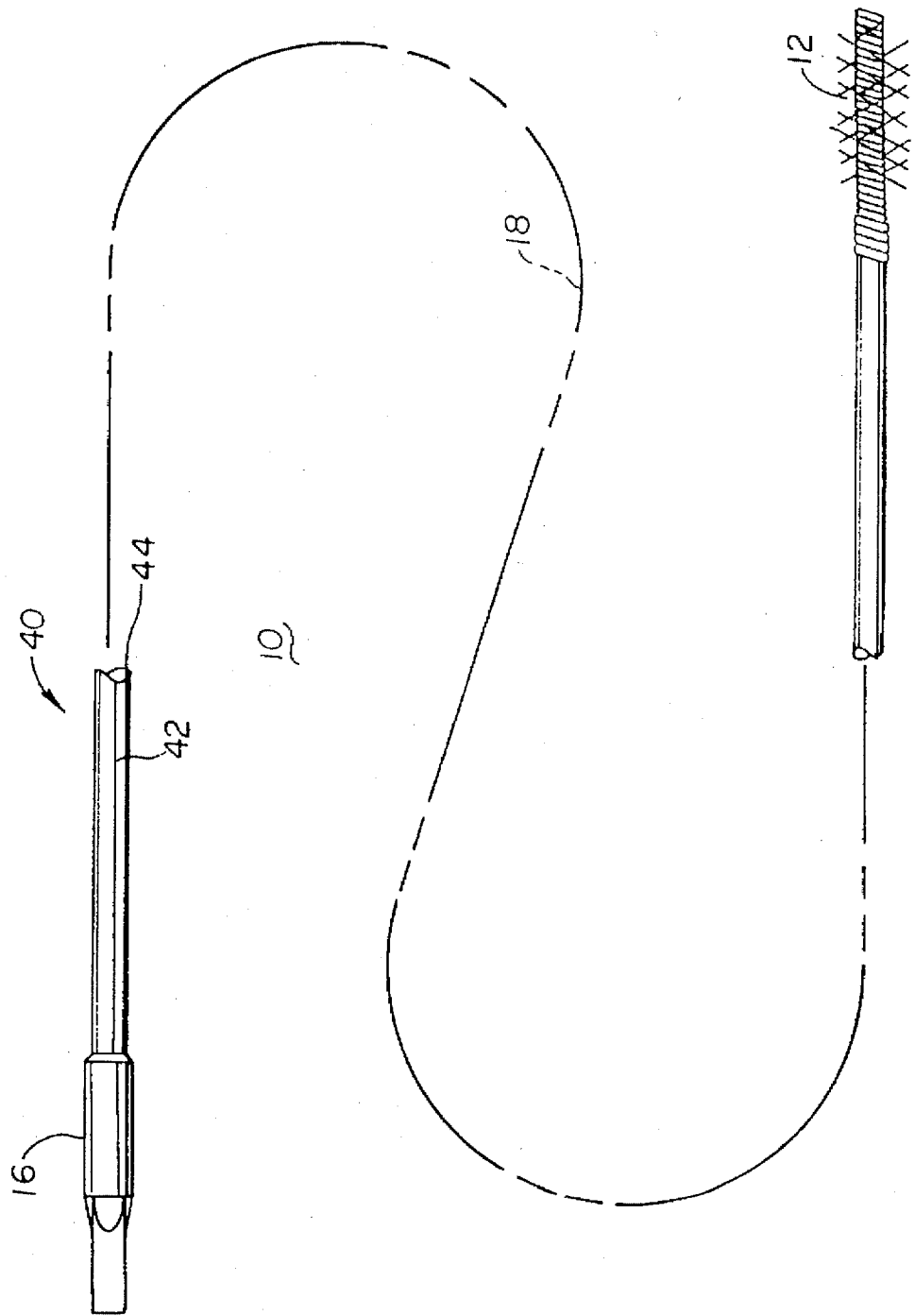
FIG. 3 is a view of the second, joined tube, embodiment of the miniaturized brush and drive shaft or body of the present invention.
Figure 4:
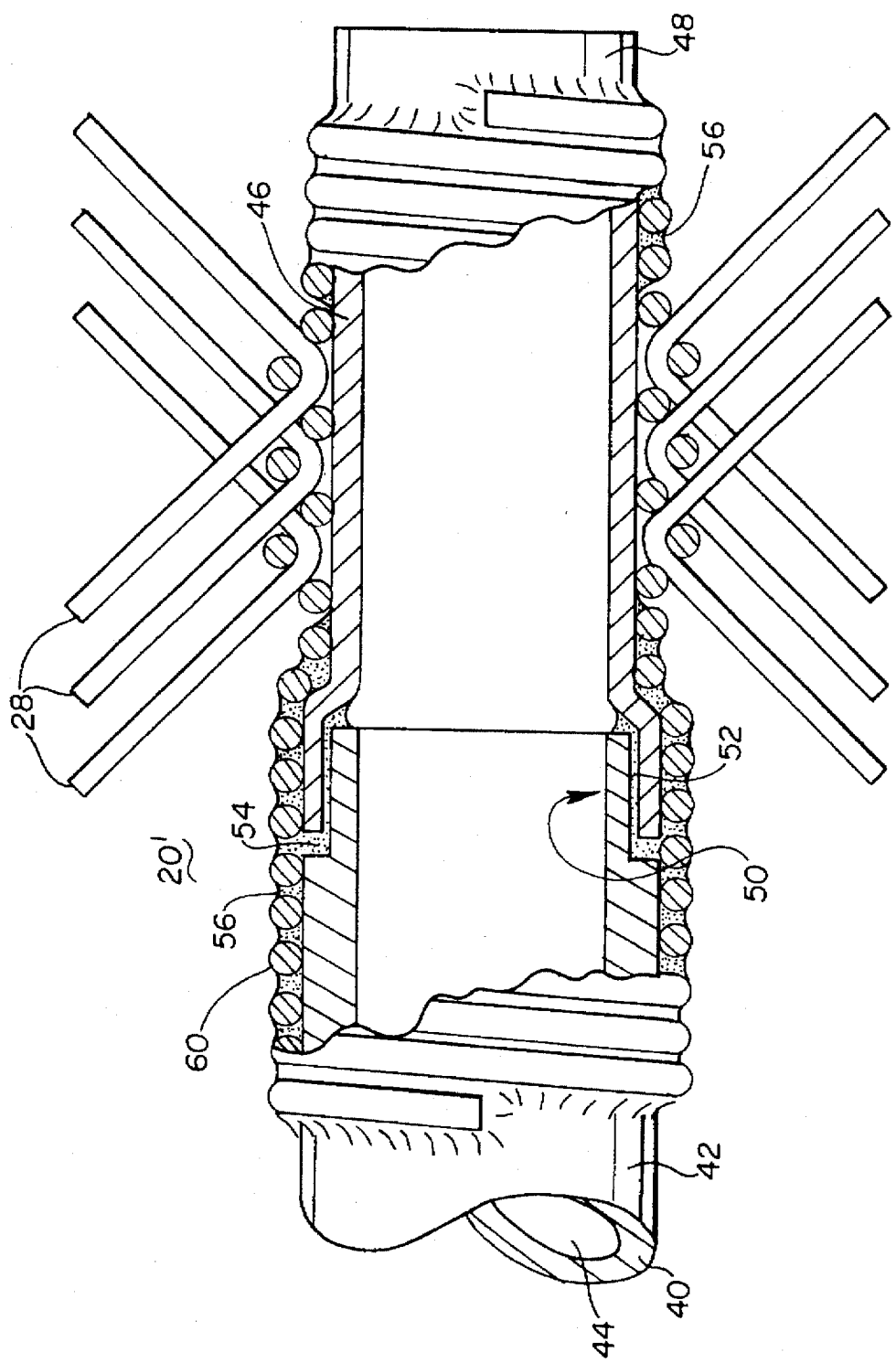
FIG. 4 is an enlarged, cross-section view of the junction of the distal tube extension and the proximal tube of FIG. 3 depicting entrapment of brush filaments between turns of the wound coil wire over the outer surface thereof.
Figure 5:
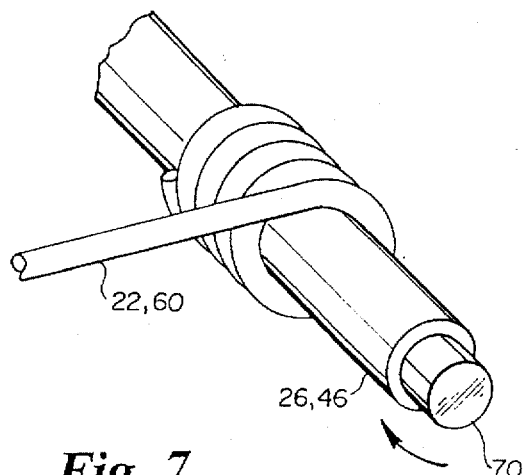
FIGS. 5–10 depict the motions of winding the coil and entrapping brush filaments about the distal tube extension of either of the embodiments of FIGS. 1–4.

Turning to FIGS. 3 and 4, the construction of the second, joined tube embodiment of the brush assembly 10' is depicted. In this embodiment, the proximal section 18 is fabricated of a proximal, elongated tube 40 having sufficient column strength to be advanced over a guide wire or through an introducer catheter and torque transfer to allow rotation of the distal brush 12 from the proximal drive hub 16. The proximal tube 40 is formed of a polymer or is formed of a stainless steel braid or wire coil reinforced polymer. The polymer is preferably urethane or nylon, and, in the latter cases, is coated over and through the openings in the stainless steel braid or coiled wire so that the inner lumen 44 and outer surface 42 are smooth and flexible. The proximal end of the proximal tube 40 is joined to the drive hub 16 having a lumen therein aligned with the lumen 44 of the proximal tube 40.

As shown in greater detail in FIG. 4, the proximal tube 40 is joined at its distal end to a separate distal tube extension 46 at a stepped ring shaped junction 50, and the brush 12 is formed over the outer surface of the tube extension 46. The proximal tube 40 has a predetermined outside diameter on the order of about 0.056 inches, a proximal tube lumen 44 inside diameter of about 0.038 inches, and a constant wall thickness through the majority of its length of about 0.009 inches. A stepped down section 52 outer diameter with reduced wall thickness is formed in a distal end portion thereof at the ring shaped junction 50. The stepped down section 52 may be achieved by grinding or heat forming the distal end of the tube 40 to the predetermined reduced outside diameter in the ring shaped junction 50.

The distal section 20' is formed of the separate distal tube extension 46 having an inside diameter corresponding to the inside diameter of the lumen 44 of the proximal tube 40. The distal tube extension 46 may be formed of nylon having the dimensions set forth above in the description of the fist embodiment. The proximal end of the distal tube extension 46 is expanded or flared to fit over the stepped down outer diameter of proximal tube 40 at junction 50. When assembled at the junction 50 as depicted in FIG. 4, there is substantially no increase in the junction outside diameter in excess of the outside diameter of the proximal tube 40. The ring shaped junction 50 may be strengthened by using adhesive or heat fusion bonds 54 at the mating surfaces thereof.

The distal, retaining coiled wire 60 is wound about the hollow tube extension outer surface 42 and about and entrapping brush bristles 28 between certain of the turns as shown in the distal section 20'. In this joined tube embodiment, the distal coiled wire 60 is continuously wrapped substantially over the full length of the distal tube extension 46, over the junction 50 and a predetermined, relatively short distance proximally from the junction 50 and over the outer wall 42. The brush bristles 28 may be entrapped along substantially all of the retaining coiled wire 60 length or just in a portion of the distal section 20' overlying the distal tube extension 46.

The junction 50 and the attachment of the coiled wire 60 may be further bonded by adhesives 56 applied between the entrapping brush filament turns and the outer surfaces 42 and 48 of the proximal tube 40 distal section and the distal tube extension 46, respectively. As described below, the bonding of the junction 50 and the attachment of the coiled wire 60 may alternatively be effected thermally. The attachment of the distal and proximal end turns of coiled wire 60 may also be secured by a bond achieved using bands of heat shrink tube applied over the turns and shrunk into a tight fit.

In either embodiment, the wire 22, 60 may be a radiopaque metal or alloy to aid in viewing the positioning of the brush assemblies 10, 10' under fluoroscopy. For increased radiopacity, the coil 22, 60 may preferably be formed of platinum or a platinum-tungsten alloy or the equivalent having an enhanced radiographic imaging characteristic. The use of such an enhanced radiopaque material is especially useful to the physician in manipulating the distal brush assemblies 10, 10'.

In both of the above described brush assemblies 10 and 10', the distal tube sections 20 and 20' may be preformed with weep holes or perforations through the side walls thereof just distal and/or proximal to the brush 12 to allow the dispersion of dissolving agents or other fluids introduced down the lumen while a guide wire is present or after it is withdrawn. The distal end opening may be provided with self sealing flaps to seal about the guide wire while the brush assembly 10, 10' is advanced or to seal the lumen end opening after the guide wire is retracted to ensure that the introduced fluid is dispersed within or proximal to the brush bristles 28. The distal end opening of the tube extension lumen may additionally or alternatively be left open to provide a fluid dispersion or flush operation distal to the brush bristles 28.

Turning now to FIGS. 5–10, they schematically depict the steps of winding the coil wire 22, 60 about and entrapping brush filaments 28 against the outer walls 32 or 42, 48 of the distal tube extensions 26 or 46 to form the brush bristles 28 in each of the above-described brush assemblies 10, 10'. In each case, a mandrel 70 is inserted down the lumens of the thin wall tube 24 or the proximal tube 40 and the lumens of the distal tube extensions 26, 46 to support them from collapsing as the coiled wire 22, 60 is wound about the outer surfaces thereof.

In the first, continuous tube embodiment, the wire 22 is first coiled over the outer surface 32 from the proximal end of thin wall tube 24 distally toward the distal tube extension 26. For purposes of illustrating this first embodiment, it will be understood that only the distal tube extension 26 and a distal coil portion of the wire 22 is shown in FIGS. 5–10. It will therefore be understood that in FIG. 5, the coiled wire 22 has been wound counter-clockwise toward the distal end section 26 by rotating the mandrel 70 and the thin wall tube 24 clockwise. When a certain number of turns are wound and the location of the proximal end of the brush is located in the distal tube extension 26, then the rotation is halted.

In regard to the second, joined tube embodiment, it will be understood that the proximal end of the coiled wire 60 is depicted in FIGS. 5–10. The coiled wire 60 is wound on the outer surface of the proximal tube 40 approximately 5–10 turns proximal to the junction 50 as depicted in FIG. 4 to reinforce the junction. It will therefore be understood that in FIG. 5, the coiled wire 60 has been wound counter-clockwise as viewed from the distal end toward and onto the surface of the distal tube extension 46 by rotating the mandrel 70 and the proximal tube 40 and distal tube extension 46 clockwise. Again, when a certain number of turns, e.g. 5–10 further turns, are wound and the location of the proximal end of the brush is located in the distal tube extension 46, then the rotation is halted.

Figure 6:
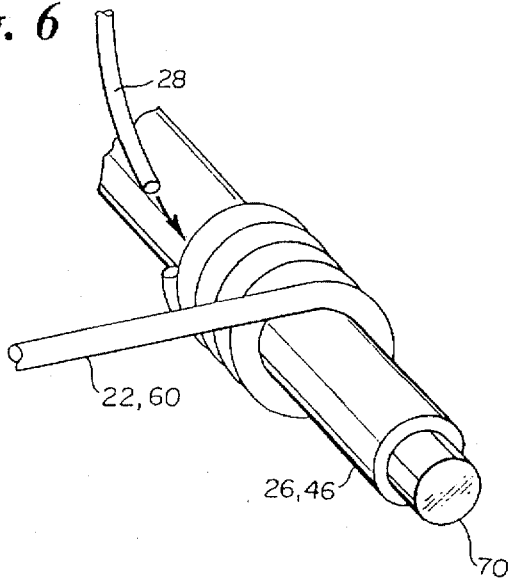
Figure 7:
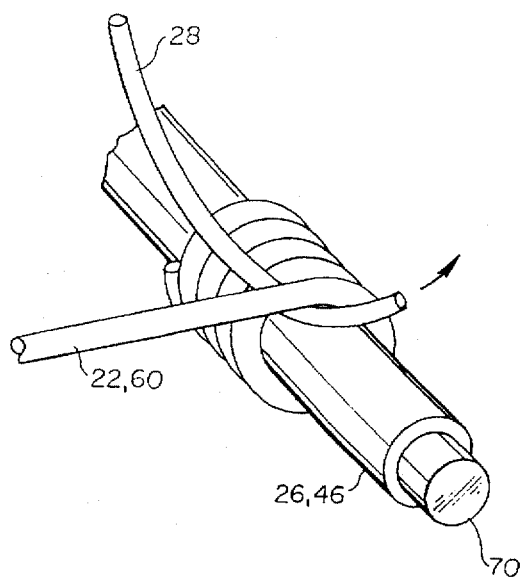
Figure 8:
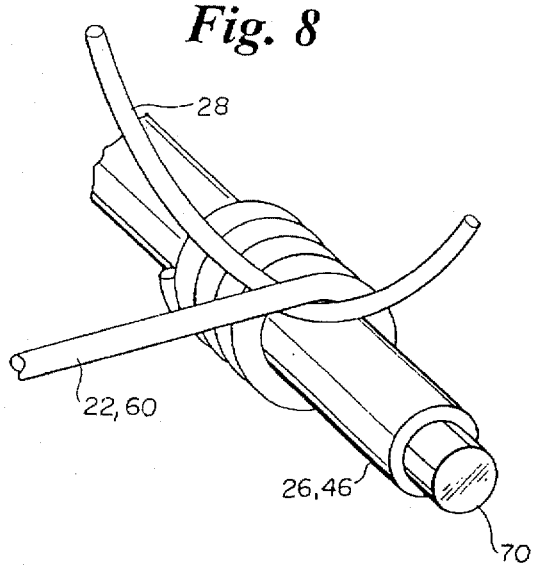
Figure 9:
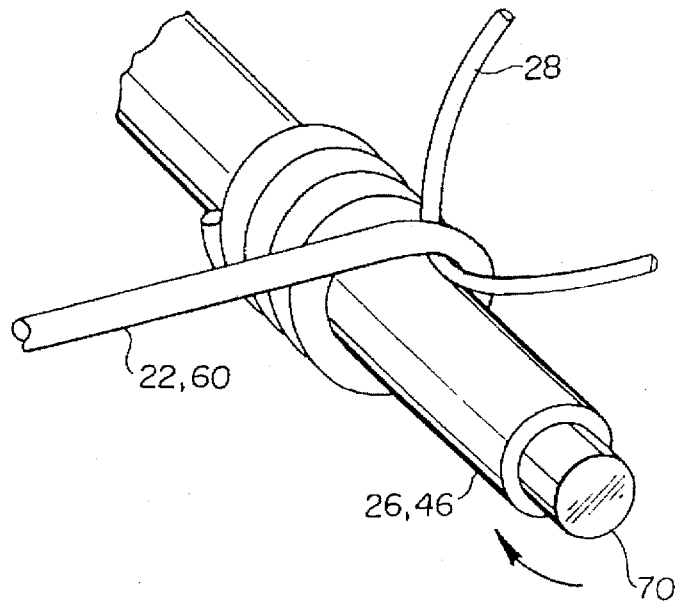
Figure 10:
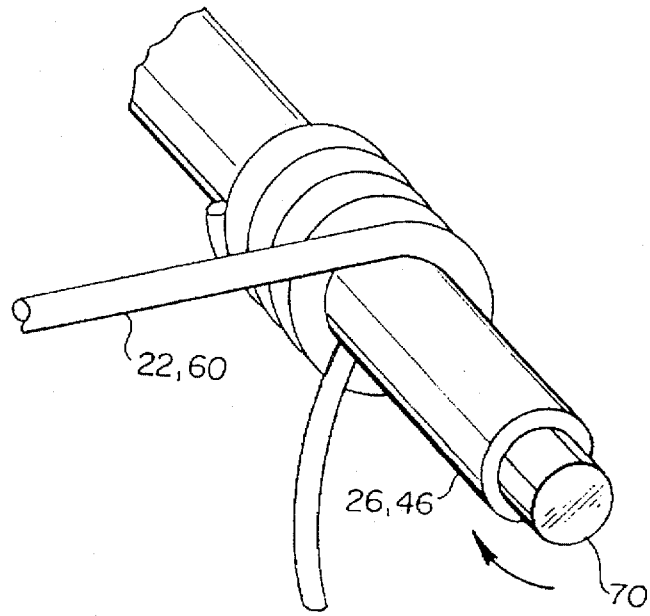

In each case, a brush filament 28 is then introduced beneath the wire 22, 60 as shown in the successive steps of FIGS. 6–8, until the filament is centered at the interface between the wire 22, 60 and the outer surface 32, 48. The rotation is then restarted as shown in FIG. 9, and the brush filament 28 is trapped between the coiled wire 22, 60 and the outer surface 32, 48 of the distal tube extension 26, 46 and the adjacent turn of the coiled wire 22, 60.

The rotation of the mandrel 70 and the distal tube extension 26, 46 continues for 180° beyond the position of FIG. 8 to the position of FIG. 10, and rotation is again halted. The next filament is inserted from above as depicted in the steps of FIGS. 6–8 and is trapped following the steps of FIGS. 9 and 10. In this manner, two brush filaments 28 are trapped for each full revolution of mandrel 70 and distal tube extension 26, 46.

The degrees of rotation between successive insertions of brush filaments 28 may vary, either more than or less than 180°, to provide for a less dense or more dense distribution of filaments 28 about the circumference of the distal tube extension 26, 46. Moreover, the insertions of the brush filaments 28 may be effected at varying degrees of rotation to provide a brush with a helical or corkscrew distribution of filaments. In other words, the brush filaments entrapped between turns of the coiled wire and the outer wall of the hollow tube extension are distributed in a helical pattern around the circumference of the outer wall to form a helical or corkscrew shaped brush.

The helix distribution may be useful in trapping a soft obstruction. In such clinical use, the brush may be rotated at a speed that effects a pumping action in the blood or fluid to attract the soft obstruction onto the bristles rather than moving it distally by the advancing brush.

The steps of FIGS. 6–10 are repeated until the requisite number of turns of the coiled wire 22, 60 complete the desired length of the brush 12. The coiled wire is then wound an additional 5–10 turns at the distal end of the distal tube extension. The coil turns are then secured at the proximal and distal ends of the brush and the proximal end of the assembly to prevent unwinding. Such securing is preferably accomplished by local application of adhesives 54 as shown in FIG. 4, but may also be accomplished by installation of short bands of thin wall heat shrink tubing or thin wall swaged metal rings or by heat fusion with the underlying thin wall tube and distal tube extension of the second embodiment and the distal tube extension of the first embodiment.

Figure 11:
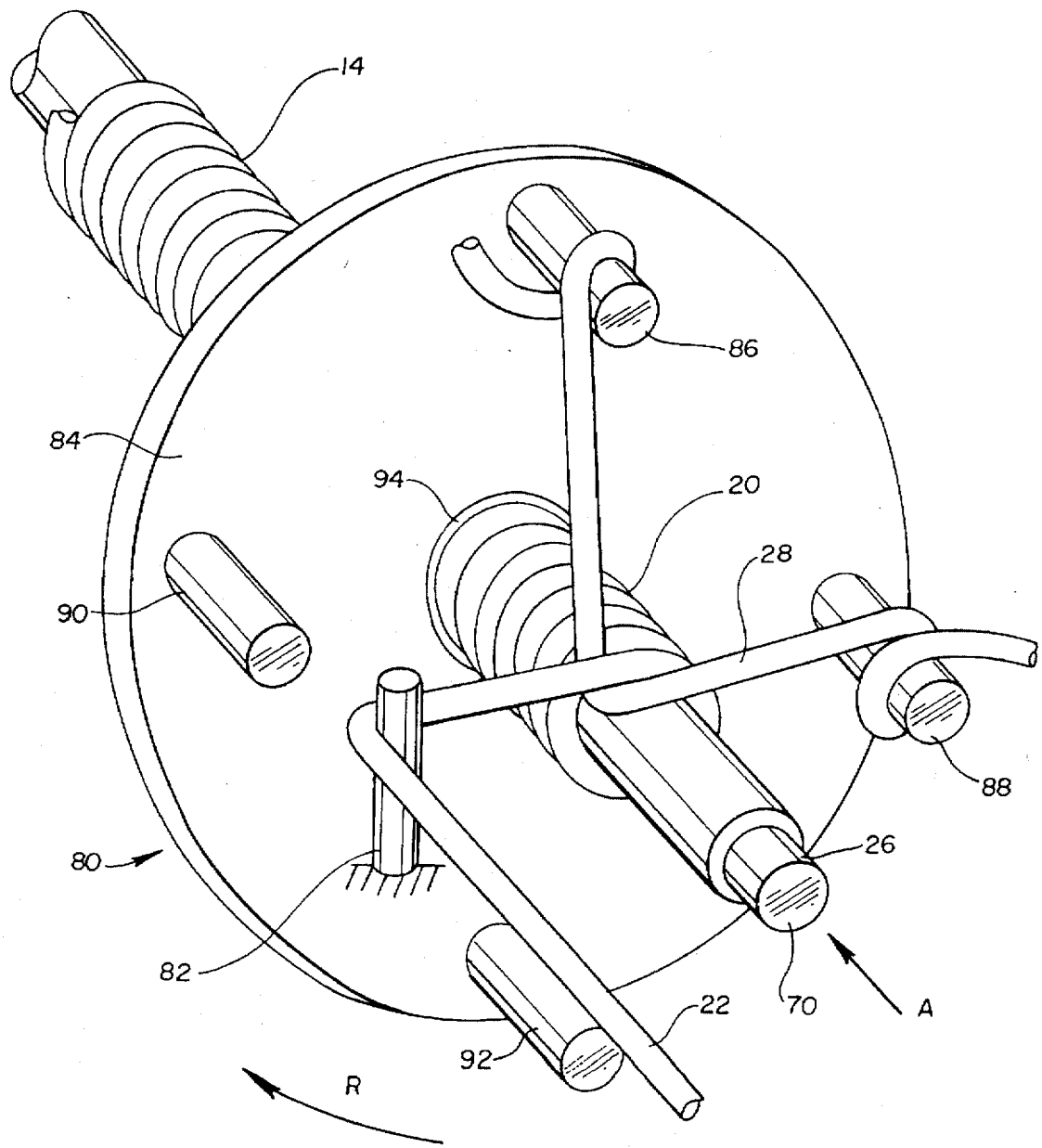
FIG. 11 is a perspective view of a fixture for entrapping brush filaments between coiled wire turns and the distal tube extension during winding of the coiled wire over the distal tube extension of the first embodiment.
Figure 12:
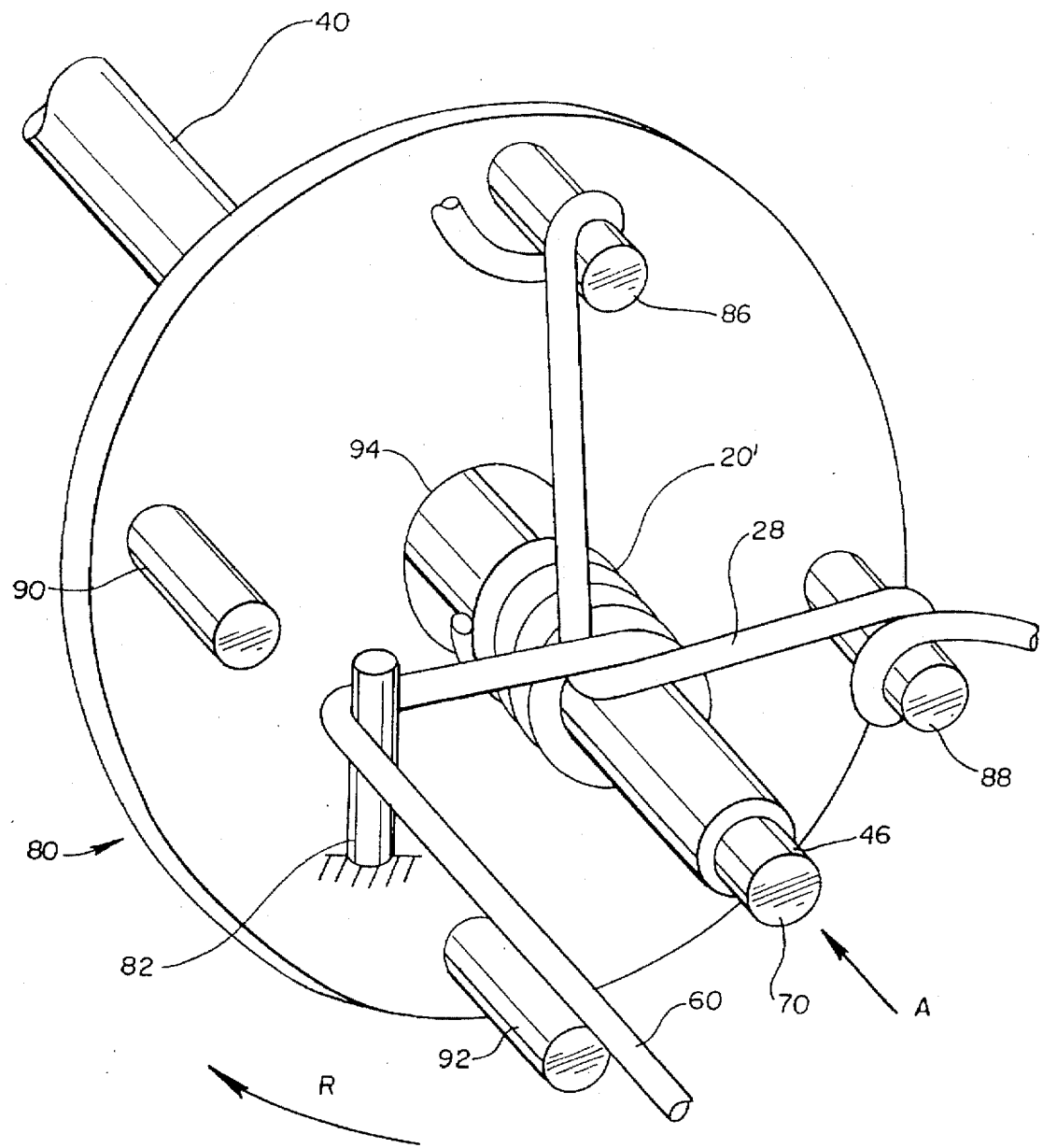
FIG. 12 is a perspective view of a fixture for entrapping brush filaments between coiled wire turns and the distal tube extension during winding of the coiled wire over the distal tube extension of the second embodiment.

In FIGS. 11 and 12, a brush bristle winding fixture 80 including a turntable 84 is shown that is employed to wind the wire 22, 60 into the coiled wire configuration over the underlying distal tube extension 26, 46 of either embodiment while the distal tube extension lumen is supported on the mandrel 70. The fixture 80 includes a fixed guide post 82 for guiding the wire 22, 60 from a supply reel (not shown) toward the distal tube extensions 26, 46 while supported on the mandrel 70. In each embodiment, the proximal tube section and the distal tube extensions 26, 46 are supported in common on the elongated mandrel 70, and the distal sections 20, 20' are inserted into the winding fixture 80 for winding of the wire 22, 60 and trapping of the brush bristle filaments 28.

FIG. 11 shows the first, continuous tube embodiment of FIGS. 1 and 2 mounted in fixture 80. In this embodiment, the wire 22 is first coiled over the outer surface 32 of the thin wall tube 24 from the proximal end distally to a point adjacent to the distal tube extension thereof on a conventional coil winding fixture. Sufficient unwound wire 22 is left attached to the distal end of the unfinished coil to be used in the fabrication of the brush using the fixture 80 and the above-described steps of FIGS. 5–10. The lumen 34 of the distal tube extension is then advanced over the mandrel 70 of fixture 80 and the remaining wire 22 is guided around fixed guide post 82 and tensioned.

In the joined tube embodiment of FIGS. 3 and 4, the distal tube extension 46 is first attached to the distal stepped down end of the tube 40 as described above. FIG. 12 shows the joined tube embodiment mounted in fixture 80 so that the distal tube extension 46, the junction 50 and a portion of the distal end of the thin wall tube 40 extend forward of the surface of the turntable 84 so that the wire 60 can be wrapped as shown in FIG. 4.

The fixture 80 also includes the turntable 84 mounted on a bearing (not shown) so that it is free to rotate. The turntable 84 has an internal clamping feature (not shown) within its bore 94 which allows it to secure the assembly of the distal tube extensions 26, 46 and the mandrel 70 (and wire coil 22 in the first embodiment as shown in FIG. 11) for rotation with the turntable 84. The clamping is effected so that the outer surfaces of the distal tube extensions 26, 46 over which the wire 22 is to be coiled (including the junction 50 of the joined tube embodiment as shown in FIG. 4) are positioned forward of the face of the turntable 22 for alignment with respect to fixed guide post 82, as shown in FIGS. 11 and 12. A further mechanism is provided for moving the assembly of the turntable 84, mandrel 70 and above-described, clamped components of the brushes to be formed axially in the direction of arrow A in synchrony with rotation of the assembly in the direction of arrow R. The wire 22, 60 is then fed over the fixed guide post 82 and wound into a coil trapping the brush filaments 28 as described above. The coil turns that are formed may be bonded with a fast acting adhesive, e.g. cyanoacrylate, to prevent slippage or unwinding.

The brush bristle filaments 28 are fed onto turntable post pairs, e.g. the posts 86 and 88 to follow the feeding and positioning steps of FIGS. 6–8 while turntable 84 and mandrel 70 are stationary. The winding of coiled wire 22, 60 follows the steps of FIGS. 9 and 10 by rotating the turntable 84 and mandrel 70 through the desired number of degrees. The ends of the depicted filament 28 may be released from the first post pair when rotation is halted, and a further brush filament may be fed onto the second turntable post pair 90 and 92 at the same time.

As described above, the distribution of filaments may be regular to form a brush with a uniform brush bristles extending from the outer wall of the hollow tube extensions or may be distributed in a pattern to form a helical or corkscrew brush.

After the brush 12 length is achieved, the retaining wire 22, 60 may be wrapped distally an additional 5–10 turns and bonded with adhesive or heat to prevent slippage or unwinding as described above. The heat bonding may be effected by heating the mandrel 70 to thermoset the coiled wire 22, 60 over the outer surface and to also seal the junction 50 of the second, joined embodiment.

The brush filaments may be trimmed to an even length to provide soft, flexible bristles extending outward from the drive shaft distal sections 20, 20'. The bristles are sufficiently resilient and dimensioned for enabling compression and passage of the brush out of and back into the distal end of an introducer catheter lumen or to be compressed and passed through a blood vessel lumen in an over the wire introduction. The bristles are effective to mix dissolving agents into the fibrin of a soft obstruction or thrombus and yet not damage the vessel wall.

Alternatively, the brush filaments may be trimmed in length in any desired pattern of long and short bristles for specific applications.

In use in the context of the above-referenced '653 patent, the brush assembly 10 or 10' is introduced through a blood vessel into proximity with a soft obstruction. A dissolving agent is introduced during rotation of the brush, either through a lumen of the introducer or the drive shaft, and out exit ports at the distal ends thereof in the region of rotation of the brush for dissolving the soft obstruction as it is contacted by the bristles.

In order to contain released fragments so that the dissolving agent may complete dissolution, the brush may be introduced through the soft obstruction downstream and rotated as the brush is slowly retracted through the obstruction. Optionally, a balloon catheter or a mesh basket may be coaxially introduced through the drive shaft lumen and placed downstream to temporarily obstruct the blood and dissolving agent flow away from the site and restrain fragments to allow the concentrated dissolving agent to complete the dissolution thereof.

Advantageously, blood clots and thrombi are more readily dissolved by the mixing action of the brush bristles as the dissolving agent is introduced. Intimal hyperplasia and the risk of vessel wall rupture or pseudoneurism is decreased by use of the soft brush bristles. The speed of dissolution may be reduced to minutes, in comparison with hours for introduction of the dissolving agent alone. The reduced amount of dissolving agent introduced decreases the risk of internal bleeding. Patient comfort is increased and cost of the intensive care treatment is reduced by the shortened time and reduction of exposure to the dissolving agent.

While the invention is preferably implemented in the brush of the type described in the above-incorporated '653 patent, it will be recognized that a miniaturized, hollow lumen brush may have other important applications and uses outside the medical device field.

In addition, while a number of preferred embodiments of the invention and variations thereof have been described in detail, other modifications and methods of using and medical applications or other applications for the same will be apparent to those of skill in the art.

Accordingly, it should be understood that various applications, modifications, and substitutions may be made of equivalents without departing from the spirit of the invention or the scope of the claims.

What is claimed is:

1. A miniaturized brush assembly comprising:

an elongated brush body formed in a proximal elongated section of a hollow tube having an inner lumen and an outer wall and a distal section comprising a hollow tube extension;

a length of coiled wire wound about the outer wall of the hollow tube extension in fixed relation thereto; and a brush formed of brush filaments, each having first and second ends and a predetermined length between the first and second ends, entrapped in a winding interface between turns of the coiled wire and the outer wall of the hollow tube extension in an entrapment zone intermediate said first and second ends to each form first and second brush bristles extending separately outward from the entrapment point to the first and second ends thereof.

2. The brush assembly of claim 1 wherein the proximal elongated section and the hollow tube extension are fabricated of a single, continuous, elongated, thin wall tube having proximal and distal ends: and the coiled wire is wound continuously over the elongated tube from the proximal to the distal end thereof, whereby the continuous coiled wire provides a structural reinforcement of the thin wall tube from the proximal end to the distal end section and the brush attached thereto.

3. The brush assembly of claim 1 wherein:

the proximal section is fabricated of a proximal elongated tube having a predetermined column strength and having a predetermined outside diameter, a proximal tube lumen inside diameter and a constant wall thickness through the majority of its length and a stepped down outer diameter with reduced wall thickness formed in a distal end portion thereof;

the distal section is formed of a separate distal extension tube having an inside diameter corresponding to the inside diameter of the proximal tube lumen, the distal extension tube having an expanded proximal end fitting over the stepped down outer diameter at a junction thereof such that the outside diameter at the junction thereof does not substantially exceed the outside diameter of the proximal tube; and the coiled wire is wound about the hollow tube extension and about and entrapping brush filaments between turns of the coiled wire in the distal section.

4. The brush assembly of claim 3 wherein the coiled wire is continuously wrapped the length of the distal tube extension, over the junction of the distal tube extension and a predetermined distance proximally from the junction.

5. The brush assembly of claim 4 wherein the junction is bonded between the entrapping brush filament turns and the outer walls of the proximal tube distal section and the distal tube extension.

6. The brush assembly of claim 4 wherein the coiled wire is formed of a metal having enhanced radiographic imaging characteristics.

7. The brush assembly of claim 1 wherein the coiled wire is formed of a metal having enhanced radiographic imaging characteristics.

8. The brush assembly of claim 1 wherein the brush filaments entrapped between turns of the coiled wire and the outer wall of the hollow tube extension are distributed in a helical pattern around the circumference of the outer wall to form a helical brush.

9. A miniaturized, rotatable brush assembly comprising:

an elongated, flexible, rotatable brush drive shaft adapted to be attached at its proximal end to a drive motor for rotating the shaft, the drive shaft being formed in a proximal elongated section of a hollow tube having an inner lumen and an outer wall and a distal section comprising a hollow tube extension;

a coiled wire wound about the outer wall of the hollow tube extension in fixed relation thereto; and a brush formed of brush filaments, each having first and second ends and a predetermined length between the first and second ends, entrapped in a winding interface between turns of the coiled wire and the outer wall of the hollow tube extension in an entrapment zone intermediate said first and second ends to each form first and second brush bristles extending separately outward from the entrapment point to the first and second ends thereof.

10. The brush assembly of claim 9 wherein the proximal elongated section and the hollow tube extension are fabricated of a single, continuous, elongated, thin wall tube having proximal and distal ends: and the coiled wire is wound continuously over the elongated tube from the proximal to the distal end thereof, whereby the continuous coiled wire provides a structural reinforcement to enhance torque transfer from the proximal end to the distal end section and the brush attached thereto.

11. The brush assembly of claim 9 wherein:

the proximal section is fabricated of a proximal elongated tube having sufficient column strength to be advanced over a guide wire or through an introducer catheter and torque transfer to allow rotation of the distal brush from the proximal end thereof and having a predetermined outside diameter, a proximal tube lumen inside diameter and a constant wall thickness through the majority of its length and a stepped down outer diameter with reduced wall thickness formed in a distal end portion thereof;

the distal section is formed of a separate distal extension tube having an inside diameter corresponding to the inside diameter of the proximal tube lumen, the distal extension tube having an expanded proximal end fitting over the stepped down outer diameter at a junction thereof such that the outside diameter at the junction thereof does not substantially exceed the outside diameter of the proximal tube; and the coiled wire is wound about the distal tube extension and about and entrapping brush filaments between the coiled wire and the distal tube extension in the distal section.

12. The brush assembly of claim 11 wherein the coiled wire is continuously wrapped the length of the distal tube extension, over the junction of the distal tube extension and a predetermined distance proximally from the junction.

13. The brush assembly of claim 11 wherein the junction is bonded between the entrapping brush filament turns and the outer walls of the proximal tube distal section and the distal tube extension.

14. The brush assembly of claim 11 wherein the coiled wire is formed of a metal having enhanced radiographic imaging characteristics.

15. The brush assembly of claim 9 wherein the coiled wire is formed of a metal having enhanced radiographic imaging characteristics.

16. The brush assembly of claim 9 wherein the brush filaments entrapped between turns of the coiled wire and the outer wall of the hollow tube extension are distributed in a helical pattern around the circumference of the outer wall to form a helical brush.

17. A method of fabricating a miniaturized, rotatable brush assembly comprising the steps of:

supporting an elongated hollow tube having an inner lumen and an outer wall and a distal section comprising a hollow tube extension over a mandrel extending through the inner lumen;

winding a coiled wire about the outer wall of the hollow tube extension in spaced coil turns;

introducing brush filaments into the winding interface between the wound coil turns and the outer wall of the hollow tube extension thereby forming a brush of entrapped brush bristles in the distal section; and withdrawing the mandrel from the inner lumen of the elongated hollow tube and tube extension.

18. The method of claim 17 further comprising the step of bonding at least a portion of the winding interface between the entrapped brush filaments, the coiled wire turns, and the outer wall of the distal tube extension.

19. The method of claim 17 wherein the proximal elongated section and the hollow tube extension are fabricated of a single, continuous, elongated, thin wall tube having proximal and distal ends: and the winding step further comprises:

winding the coiled wire continuously over the elongated tube from the distal end to the proximal end thereof, whereby the continuous coiled wire provides a structural reinforcement in the proximal elongated section to enhance torque transfer from the proximal end to the distal end section and the brush attached thereto.

20. The method of claim 19 further comprising the step of bonding between the entrapped brush filaments, the coiled wire turns, and the outer wall of the distal tube extension.

21. The method of claim 17 wherein the recited steps are preceded by the step of forming the elongated hollow tube having an inner lumen and an outer wall and a distal section comprising a hollow tube extension comprising the further steps of:

fabricating the proximal section of a proximal elongated tube having sufficient column strength to be advanced over a guide wire or through an introducer catheter and torque transfer to allow rotation of the distal brush from the proximal end thereof and having a predetermined outside diameter, a proximal tube lumen inside diameter and a constant wall thickness through the majority of its length;

forming a stepped down outer diameter with reduced wall thickness in a distal end portion of the proximal elongated tube;

forming a separate distal extension tube having an inside diameter corresponding to the inside diameter of the proximal tube lumen;

expanding a proximal end lumen of the distal extension tube and fitting the expanded lumen over the stepped down outer diameter at a junction thereof such that the outside diameter at the junction thereof does not substantially exceed the outside diameter of the proximal tube; and wherein said winding step further comprises:

winding the coiled wire about the distal tube extension in the distal section.

22. The method of claim 21 wherein said winding step further comprises winding the coiled wire continuously along the length of the distal tube extension, over the junction of the distal tube extension and a predetermined distance proximally from the junction.

23. The method of claim 22 further comprising the step of bonding the junction between the expanded lumen and the stepped down outer diameter.

24. The method of claim 22 further comprising the step of bonding the coiled wire turns and the outer wall of the distal tube extension.

25. The method of claim 21 further comprising the step of bonding the junction between the expanded lumen and the stepped down outer diameter.

26. The method of claim 17 wherein the introducing step further comprises distributing the brush filaments to be entrapped between turns of the coiled wire and the outer wall of the hollow tube extension in a helical pattern around the circumference of the outer wall to form a helical brush.

27. The method of claim 17 wherein the coiled wire is formed of a metal having enhanced radiographic imaging characteristics.

* * * * *